(12) United States Patent
Hong et al.

(10) Patent No.: US 8,211,172 B2
(45) Date of Patent: Jul. 3, 2012

(54) CORRECTION OF HIGHER ORDER ABERRATIONS IN INTRAOCULAR LENSES

(75) Inventors: Xin Hong, Arlington, TX (US); Mutlu Karakelle, Fort Worth, TX (US); Xiaoxiao Zhang, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/971,125

(22) Filed: Dec. 17, 2010

(65) Prior Publication Data

US 2011/0085133 A1  Apr. 14, 2011

Related U.S. Application Data

(63) Continuation of application No. 11/435,905, filed on May 17, 2006, now Pat. No. 7,879,089.

(51) Int. Cl.
*A61F 2/16* (2006.01)

(52) U.S. Cl. ............................. 623/6.11; 623/4.1

(58) Field of Classification Search .......... 351/205, 351/246, 177; 623/6.11, 4.1, 6.23, 6.24, 623/5.11, 6.37, 6.34, 901
See application file for complete search history.

(56) References Cited

U.S. PATENT DOCUMENTS

| | | | |
|---|---|---|---|
| 5,282,852 A | 2/1994 | Capetan et al. | |
| 5,699,142 A | 12/1997 | Lee et al. | |
| 6,609,793 B2 | 8/2003 | Norrby et al. | |
| 6,705,729 B2 | 3/2004 | Piers et al. | |
| 6,740,116 B2 | 5/2004 | Morcher | |
| 7,111,938 B2 | 9/2006 | Andino | |
| 7,150,759 B2 | 12/2006 | Paul et al. | |
| 7,762,667 B2 | 7/2010 | Andino | |
| 7,775,663 B2 | 8/2010 | Andino | |
| 7,780,293 B2 | 8/2010 | Andino | |
| 2002/0105617 A1 | 8/2002 | Norrby et al. | |
| 2004/0156014 A1 | 8/2004 | Piers et al. | |
| 2005/0203619 A1 | 9/2005 | Altmann | |
| 2006/0030938 A1 | 2/2006 | Altmann | |
| 2006/0167545 A1 | 7/2006 | Fiala et al. | |

FOREIGN PATENT DOCUMENTS

| | | |
|---|---|---|
| EP | 1390802 A1 | 2/2004 |
| EP | 1857077 | 11/2007 |
| RU | 2186417 | 7/2002 |
| WO | WO 2005/098518 | 4/2005 |
| WO | WO 2005/046527 | 5/2005 |

OTHER PUBLICATIONS

Larry Thibos, Xin Hong, Arthur Bradley and Xu Cheng "Statistical Variation of Aberration Structure and Image Quality in a Normal Population of Healthy Eyes," Journal of the Optical Society of America, vol. 19, No. 12, p. 2329-2348, Dec. 2002.

(Continued)

*Primary Examiner* — Hung Dang
(74) *Attorney, Agent, or Firm* — Johnathan E. Prejean

(57) ABSTRACT

In one aspect, the present invention provides a method of designing an intraocular lens (IOL) to address variations of at least one ocular parameter in a population of patient eyes. The method can include establishing at least one eye model in which the ocular parameter can be varied over a range exhibited by the population. The eye model can be employed to evaluate a plurality of IOL designs in correcting visual acuity for eyes in the patient population. An IOL design that provides a best fit for visual performance over at least a portion of the parameter range can then be selected.

10 Claims, 14 Drawing Sheets

OTHER PUBLICATIONS (English translation) Zykov, et. al., "Experimental Model of the Eye for Testing Intraocular Lenses and Demonstrations"; Materials from the conference "Biomechanics of the Eye," 2005, pp. 186-190; Note: English translation is 9 pages.

(English translation) Lenkova, "Influence of the Optical Parameters of the Eye on the Choice of the Refraction of Monofocal and Biofocal Intraocular Lenses"; Autometria, 2001, No. 5, pp. 96-102; English translation is 9 pages.

Almann et al., "Optical performance of 3 intraocular lens designs in the presence of decentration," Journal of Cataract & Refractive Surgery—Laboratory Science, Mar. 31, pp. 574 to 585, Mar. 2005.

Gobbi et al.; Optomechanical eye model with imaging capabilities for objective evaluation on intraocular lenses; Journal of Cataract & Refractive Surgery—Laboratory Science, vol. 32, Issue No. 4, pp. 643 to 651, Apr. 2006.

EFFECTS OF CORNEAL RADIUS

EFFECTS OF CORNEAL RADIUS

EFFECTS OF CORNEAL ASPHERICITY

EFFECTS OF CORNEAL ASPHERICITY

EFFECTS OF ACD

EFFECTS OF ACD

POPULATION DISTRIBUTIONS OF MTF VALUES

CORRECTION OF HIGHER ORDER ABERRATIONS IN INTRAOCULAR LENSES

CROSS-REFERENCE TO RELATED APPLICATION

This application is a Continuation (CON) of Allowed U.S. application Ser. No. 11/435,905, filed May 17, 2006, now U.S. Pat. No. 7,879,089, priority of which is claimed under 35 U.S.C. §120, the contents of which are incorporated herein by reference.

BACKGROUND

The present invention relates generally to methods of designing ophthalmic lenses, and more particularly to such methods that take into account variations of ocular parameters within a population.

Intraocular lenses (IOLs) are routinely implanted in patients' eyes during cataract surgery to replace the natural crystalline lens. Such lenses are typically designed by employing simplified eye models that do not necessarily provide an accurate representation of the human eye anatomy. In some cases, a relatively accurate eye model representing an average human eye is established for the design process. However, such an average eye model cannot be utilized to consider variations in performance of the lens across a population of patients whose eyes can exhibit differing ocular parameters.

Accordingly, there is a need for better methods for designing ophthalmic lenses, and in particular IOLs.

SUMMARY

The present invention is generally directed to methods of designing intraocular lenses (IOLs) that account for variations of one or more ocular parameters, such as, ocular axial length or corneal asphericity, within a population of patient eyes for which the IOL is intended. By way of example, such a method can arrive at a final IOL design by considering visual performance (e.g., visual acuity and/or contrast sensitivity) achieved by a plurality of IOL designs—generated, e.g., by varying a lens design parameter—in a model eye in which at least one ocular parameter can be varied. In some cases, the IOL design that provides the best fit for visual performance over at least a portion of an ocular parameter range exhibited by the population is selected. The best fit visual performance can be determined, for example, by evaluating the average of weighted visual performance for each IOL design across the ocular parameter range. The weighting of the visual performance can be based, e.g., on the distribution of the ocular parameter values over the population.

In one aspect, the invention provides a method of designing an IOL to address variations of at least one ocular parameter in a population of patient eyes. The method can include establishing at least one eye model in which the ocular parameter can be varied over a range exhibited by the population. The eye model can be employed to evaluate a plurality of IOL designs in correcting visual performance of eyes in the patient population. An IOL design that provides a best fit for visual performance (e.g., visual acuity or contrast sensitivity) over at least a portion of the range exhibited by the population can then be selected. By way of example, in this manner, a series of IOL designs can be selected such that each individual design provides the best visual performance for a portion of the population of patient eyes.

In a related aspect, the method calls for applying a weighting function to visual performance exhibited by the IOL designs. The weighting function can be based, e.g., on distribution of the ocular parameter values within the population. For example, the visual performance exhibited by the eye model at a more probable value of the ocular parameter can be given a greater weight than that at a less probable value. The best fit for visual performance can be determined as an optimal value of the weighted visual acuity among the IOL designs.

In a related aspect, the IOL designs can be generated by varying at least one lens design parameter. By way of example, the lens design parameter can be a conic constant of an aspherical surface of the lens, two conic constants associated with a toric surface of the lens, an apodization function associated with step heights at zone boundaries of a diffractive pattern disposed on a lens surface, or any other lens parameter of interest.

In a related aspect, the visual performance associated with an eye model incorporating an IOL design can be obtained by determining a modulation transfer function at the retina of the eye model. By way of example, the modulation transfer function can be calculated theoretically by employing ray-tracing techniques.

In another aspect, the ocular parameter can include, for example, ocular axial length, corneal asphericity (e.g., a conic constant characterizing the corneal asphericity), corneal radius and/or ocular anterior chamber length.

In other aspects, a method of designing an IOL is disclosed that includes generating a human eye model in which at least one ocular biometric parameter can be varied. The method further calls for evaluating the optical performance of a plurality of IOL designs by incorporating the designs in the eye model and varying the ocular parameter over at least a portion of a range exhibited by eyes in a patient population. At least one of the IOL designs that provides an optimal performance can then be selected.

The ocular parameter can comprise, for example, any of the corneal radius, corneal sphericity, anterior chamber depth or ocular axial length. Further, the IOL designs can be generated by varying at least one lens design parameter, e.g., by employing a Monte Carlo simulation. Some examples of such lens design parameters include, without limitation, a conic constant of an aspherical lens surface, two conic constants associated with a toric lens surface or an apodization function associated with step heights at zone boundaries of a diffractive pattern disposed on a lens surface.

In a related aspect, the optical performance of an IOL design can be evaluated by employing the eye model to determine an average visual performance (e.g., visual acuity) provided by that design over the ocular parameter range. By way of example, the visual performance exhibited by an IOL design at a given value of the ocular parameter can be determined by calculating a modulation transfer function at the retina of the eye model incorporating the design. The visual performance values calculated for a number of different values of the ocular parameter within a range of interest can then be averaged to generate an average visual performance. In some cases, the evaluation of the optical performance of an IOL design is based on a weighted average visual acuity determined for that design, e.g., in accordance with probability distribution of the values of the ocular parameter over the range exhibited by the population. The IOL exhibiting the greatest weighted visual performance can then be identified as the one providing an optimal performance.

In another aspect, a method of designing a family of intraocular lenses (IOLs) is disclosed that includes establishing at least one eye model in which at least one ocular parameter can be varied over a range exhibited by a population of patients. The eye model can then be employed to evaluate a plurality of IOL designs for visual performance for eyes in the patient population. At least two of the IOL designs can be selected such that one design provides the best fit visual performance (e.g., based on visual acuity and/or image contrast) for one portion of the population and the other provides the best fit visual performance for another portion of the population. The ocular parameter can be, for example, corneal radius, corneal asphericity, anterior chamber depth, or axial length. By way of example, in one embodiment, three IOL designs can be selected, each for one portion of a population, such that one IOL design exhibits an spherical aberration of about −0.1 microns, while the other two exhibit, respectively, spherical aberrations of about −0.2 and about −0.3 microns.

In another aspect, the invention provides a method of modeling visual performance of an ophthalmic lens, e.g., an IOL, which includes establishing a model eye that incorporates the ophthalmic lens and determining a modulation transfer function (MTF) at a retinal plane of that model eye. At least one MTF value corresponding to a low spatial frequency can then be utilized to evaluate a contrast sensitivity of that model eye. The low spatial frequency can be, e.g., a spatial frequency less than about 60 lp/mm (~18 cycles/degree or 20/33 letter acuity). By way of example, the low spatial frequency can be in a range of about 5 to about 60 lp/mm (~1.5 to 18 cycles/degree). Further, at least one MTF value corresponding to a high spatial frequency can be utilized to evaluate a visual acuity of the model eye. The high spatial frequency can be, e.g., a spatial frequency greater than about 60 lp/mm (~18 cycles/degree). For example, the high spatial frequency can be in a range of about 60 lp/mm to about 100 lp/mm (~18 to 30 cycles/degree).

In another aspect, a method of modeling visual performance of an ophthalmic lens, e.g., an IOL, is disclosed that includes establishing a model eye that incorporates the ophthalmic lens and determining a modulation transfer function (MTF) at a retinal plane of that model eye. At least one MTF value corresponding to a high spatial frequency can then be utilized to evaluate a visual acuity of the model eye. The high spatial frequency can be, e.g., a frequency greater than about 60 lp/mm (~18 cycles/degree). For example, the high spatial frequency can be in a range of about 60 to about 100 lp/mm (~18 to 30 cycles/degree).

In yet another aspect, estimates of manufacturing tolerance associated with one or more lens characteristics can be incorporated in the IOL design. This allows the visual performance calculations to take into account variations of certain lens properties that can occur during manufacturing. Some examples of lens characteristics, which can be subject to statistical variations due to manufacturing tolerances, include irregularities imparted to one or more lens surfaces, the radius of one or more lens surfaces, the lens thickness, or the degree of asphericity exhibited by one or more lens surfaces.

In another aspect, a method is disclosed for providing an IOL for implantation in a patient's eye characterized by an ocular parameter within a range exhibited by eyes of patients in a population. The method includes providing a plurality of IOLs having variations in at least one lens design parameter, and selecting of the IOLs that provides a best fit for visual performance over at least a portion of the ocular parameter range for implantation in the patient's eye.

In a related aspect, in the above method, the selection of the IOL further comprises determining visual performance exhibited by each IOL for a plurality of ocular parameter values within the range of values exhibited by the eyes of patients in the population. A weighted average visual performance for each IOL based on a probability distribution of the ocular parameter in the population can then be generated, and the best fit for visual performance can be identified as a maximum value of the weighted average visual performance across the lens designs.

Some examples of ocular parameters whose variations can be considered in the above method of providing an IOL include, without limitation, corneal radius, corneal asphericity, anterior chamber depth, ocular axial length, and a deviation of line of sight from an optical axis of the eye.

Further understanding of the invention can be obtained by reference to the following detailed description in conjunction with the associated drawings, which are briefly described below:

DETAILED DESCRIPTION OF THE PREFERRED EMBODIMENTS

The present invention generally provides methods for designing ophthalmic lenses (e.g., IOLs) by simulating the performance of a plurality of lenses in model eyes characterized by different values of selected ocular parameters based on variations of those parameters exhibited in a population of patient eyes. In the embodiments that follow, the salient features of various aspects of the invention are discussed in connection with intraocular lenses. However, the teachings of the invention can also be applied to other ophthalmic lenses, such as contact lenses. The term "intraocular lens" and its abbreviation "IOL" are used herein interchangeably to describe lenses that are implanted into the interior of the eye to either replace the eye's natural lens or to otherwise augment vision regardless of whether or not the natural lens is removed. Intracorneal lenses and phakic lenses are examples of lenses that may be implanted into the eye without removal of the natural lens.

Figure 1:
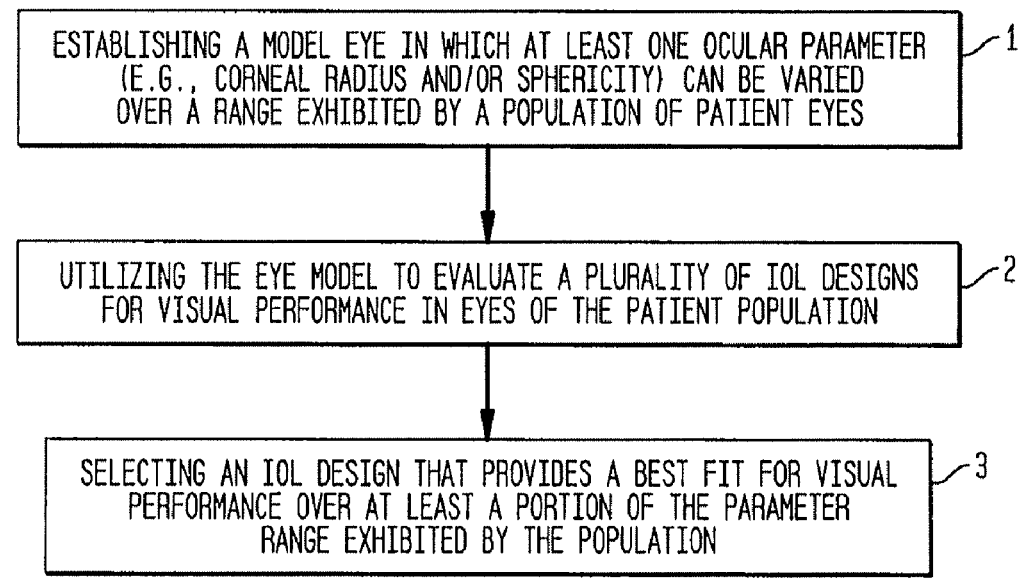
FIG. 1 is a flow chart depicting various steps in an exemplary embodiment of a method according to the teachings of the invention for designing an IOL.

With reference to a flow chart of FIG. 1, in one embodiment of a method for designing an intraocular lens (IOL), in an initial step 1, an eye model is established in which at least one ocular parameter (e.g., corneal radius or sphericity) can be varied. In many embodiments, the eye model is a theoretical model that facilitates varying one or more of the ocular parameters, though a physical eye model can also be utilized. The eye model can then be employed to evaluate a plurality of IOL designs in correcting visual performance for eyes in a patient population of interest (step 2). Based on the evaluations of the IOL designs, in step 3, at least one of the designs can be selected that provides a best fit for visual performance over at least a portion of a range (or preferably the entire range) of values exhibited for that ocular parameter in that patient population.

In many embodiments, the optical performance of each IOL design can be evaluated by calculating a modulation transfer function (MTF) associated with the eye model in which that IOL design is incorporated. As known in the art, an MTF provides a quantitative measure of image contrast exhibited by an optical system, e.g., an eye model comprising an IOL. More specifically, the MTF of an imaging system can be defined as a ratio of a contrast associated with an image of an object formed by the optical system relative to a contrast associated with the object.

The human visual system utilizes most spatial frequencies resolvable by neural sampling. Thus, in many embodiments, the MTF values ranging from low (e.g., 10 lp/mm, corresponding to about 20/200 visual acuity) to high (e.g., 100 lp/mm, corresponding to about 20/20 visual acuity) are averaged to obtain measure of an expected optical performance of an IOL design implanted in a human eye.

In the exemplary embodiments discussed below, an average MTF is employed as a merit function to determine an optimal focal plane and to assess the optical quality of a particular hypothetical eye model in Monte Carlo simulations.

The Monte Carlo analysis can be configured to simulate random variability associated with values of various ocular parameters among different patients. By way of example, human eyes exhibit variable corneal power, corneal spherical aberration, anterior chamber depth, and axial length. Further, the natural crystalline lens, and/or an implanted IOL, can have various amounts of rotation, decentration and/or tilt, e.g., relative to an optical axis of the eye. The variations are randomly, and generally normally, distributed. In many embodiments, the Monte Carlo analysis selects values from a normal probability distribution associated with one or more of these variables (e.g., a joint probability distribution corresponding to a plurality of variables) to generate a plurality of hypothetical human eyes belonging to a population of interest. The optical quality of each eye model as indicated, for example, by an average MTF, can then be computed. In some embodiments, the eye model having the best average MTF can be chosen as the most suitable design for that population. Further, the MTF values can be aggregated to provide statistics, such as mean, standard deviation, 10 percentile, 50 percentile and 90 percentile.

In addition to biometric parameters, variations due to other factors, such as misalignment errors (e.g., decentration, tilt and/or rotation) and defocus, can also be considered in simulating the optical performance of a plurality of IOLs.

Figure 2:
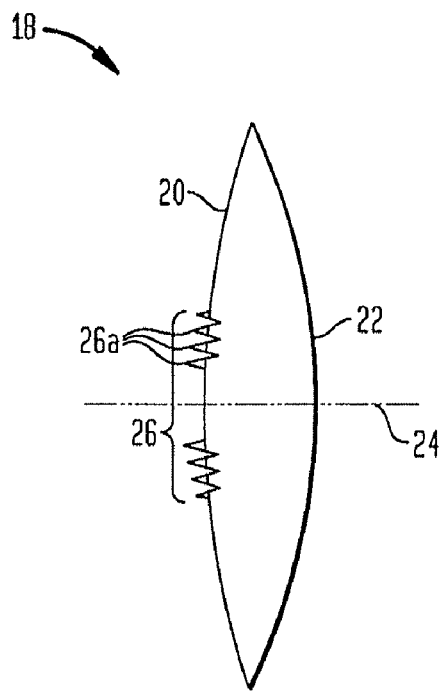
FIG. 2 is a schematic cross-sectional view of a hypothetical diffractive lens whose performance across a population of interest can be evaluated by incorporation in an eye model and varying selected ocular parameters of the model.

To further illustrate various aspects of the invention, the optical performance of each of a plurality of hypothetical and exemplary lens designs was evaluated by varying selected ocular parameters of an eye model in which the lens design was incorporated. With reference to FIG. 2, each lens was assumed to include an optic 18 having an anterior optical surface 20 and a posterior optical surface 22 disposed about an optical axis 24. The anterior surface includes a diffraction pattern 26 formed of a plurality of diffractive zones 26a, which are separated from one another by steps whose heights decrease as their distances from the optical axis increase. By way of example, the step heights can be defined in accordance with the following relation:

$$\text{Step height} = \frac{p\lambda}{n_2 - n_1} f_{apodize} \quad \text{Eq. (1)}$$

wherein,
p is a phase height,
$\lambda$ is a design wavelength (e.g., 550 nm),
$n_2$ is the refractive index of the material forming the lens, and
$n_1$ is the index of refraction of the medium surrounding the lens,
$f_{apodize}$ denotes an apodization function.

A variety of apodization functions can be employed. For example, in some embodiments, the apodization function is defined in accordance with the following relation:

$$f_{apodize} = 1 - \left\{ \frac{(r_i - r_{in})}{(r_{out} - r_{in})} \right\}^{exp}, \quad r_{in} \le r_i \le r_{out} \quad \text{Eq. (4)}$$

wherein
$r_i$ denotes the distance of each radial zone boundary from the intersection of the optical axis with the surface,
$r_{in}$ denotes the inner boundary of the apodization zone,
$r_{out}$ denotes the outer boundary of the apodization zone, and
exp denotes an exponent to obtain a desired reduction in the step heights. Further details regarding apodization of the step heights can be found, e.g., in U.S. Pat. No. 5,699,142, which is herein incorporated by reference.

Moreover, a base profile of the anterior surface has an aspherical base profile characterized by a selected degree of asphericity while the posterior surface exhibits a selected degree of toricity. A reference hypothetical design was also considered in which the anterior surface is spherical (i.e., it lacks asphericity). The various structural parameters of these hypothetical designs (i.e., anterior surface radius (ASR), anterior surface asphericity (ASC), posterior surface radius at one meridian (BSR1), posterior surface radius at another steeper meridian (BSR2), the center thickness (CT), power, and toricity) are summarized in Table 1 below:

TABLE 1

| Design | ASR (mm) | ASC | BSR1 (mm) | BSR2 (mm) | CT | Power (D) | Toricity |
|---|---|---|---|---|---|---|---|
| #1 | 20.74 | −13.44 | −22.33 | −19.35 | 0.646 | 21 | T3 (1.5) |
| #2 | 20.74 | −20.44 | −22.33 | −19.35 | 0.646 | 21 | T3 (1.5) |
| #3 | 20.74 | −28.51 | −22.33 | −19.35 | 0.646 | 21 | T3 (1.5) |
| #4 | 20.74 | −37.99 | −22.33 | −19.35 | 0.646 | 21 | T3 (1.5) |
| #5 | 20.74 | −47.36 | −22.33 | −19.35 | 0.646 | 21 | T3 (1.5) |
| Reference | 13.50 | 0 | −50.10 | −37.14 | 0.646 | 21 | T3 (1.5) |

For the purposes of this illustration, the aforementioned biometric, misalignment and refractive error parameters were considered as independent and uncorrelated variables in a joint statistical distribution. For each simulation run, different values of these parameters were chosen randomly and independently so as to construct an eye model that would simulate an individual arbitrary eye in the general population. The optical performance of such an eye model with each of the above hypothetical IOL designs was evaluated by calculating the MTF. An optical design software marketed as Zemax® (version Mar. 4, 2003, Zemax Development Corporation, San Diego, Calif.) was utilized to calculate the MTF. This process of random selection and optical modeling was iterated 200 times, to provide statistics regarding performance of each design across the population. It should be understood that these simulations are presented only for illustrative purposes and are not intended to limit the scope of the invention. For example, in other embodiments, the number of iterations can be much larger than 200 (or less than 200).

By way of example, in the above simulations, the corneal radius was assumed to be normally distributed above an average value of about 7.72 mm with a standard deviation of +/−0.28 mm. Further, the values of corneal asphericity (conic constant) were selected from a normal distribution having an average value of −0.183 and a standard deviation of +/−0.160. The anterior chamber depth was assumed to be distributed about an average value of 4.60 mm with a standard deviation of +/−0.30 mm.

Figure 3A:
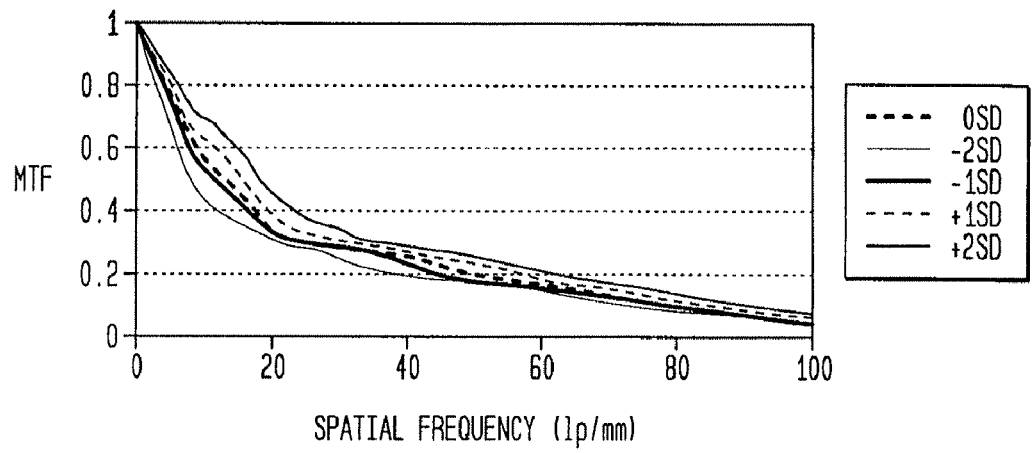
FIG. 3A shows a plurality of MTFs calculated in an exemplary embodiment of a method of the invention for a plurality of eye models characterized by different corneal radii in which a hypothetical IOL design was incorporated.
Figure 3B:
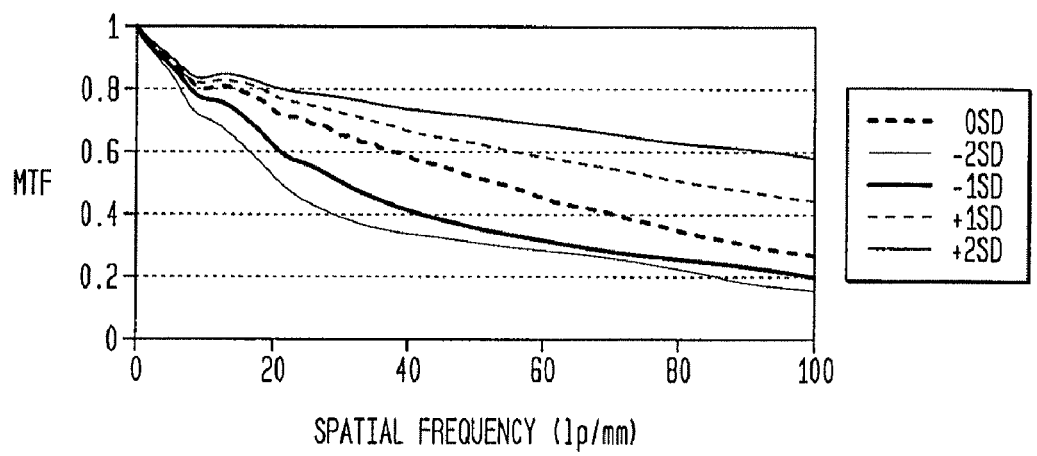
FIG. 3B shows a plurality of MTFs calculated in an exemplary embodiment of a method of the invention for a plurality of eye models characterized by different corneal radii in which another (reference) hypothetical IOL was incorporated.

By way of example, FIG. 3A shows a plurality of MTFs calculated for eye models characterized by five different corneal radii (i.e., 7.16 mm (−2 SD (standard deviation)), 7.44 (−1 SD), 7.72 mm (0 SD), 8.00 (+1 SD) and 8.28 (+2 SD)), in which the above hypothetical IOL identified as Design #3 was incorporated. A corneal asphericity of −0.183 was employed for all the eye models. Moreover, FIG. 3B presents respective MTFs exhibited by the same eye models, in which the above hypothetical IOL designated as reference was incorporated. The calculations were performed by utilizing a 6.0 mm entrance pupil. These calculations show that the performance of the IOL (design #3) having an aspherical anterior surface is more susceptible to variations in the corneal radius than that of the reference lens that lacks such asphericity.

As noted above, the corneal asphericity (typically expressed as conic constant) is another parameter that was varied in the illustrative Monte Carlo simulations. A number of studies show that the distributions of corneal sphericity typically follow bell-curved shapes. A small portion of corneas are substantially aberration-free (characterized by a conic constant of 0.5) and a small portion are spherical (characterized by a conic constant of 0). Most anterior corneas exhibit a corneal sphericity that lies within one standard deviation of 0.16 about an average value of −0.183. In other words, the average spherical aberration exhibited by a cornea within the general population is about 0.242 microns with a standard deviation of about 0.086 microns.

Figure 4A:
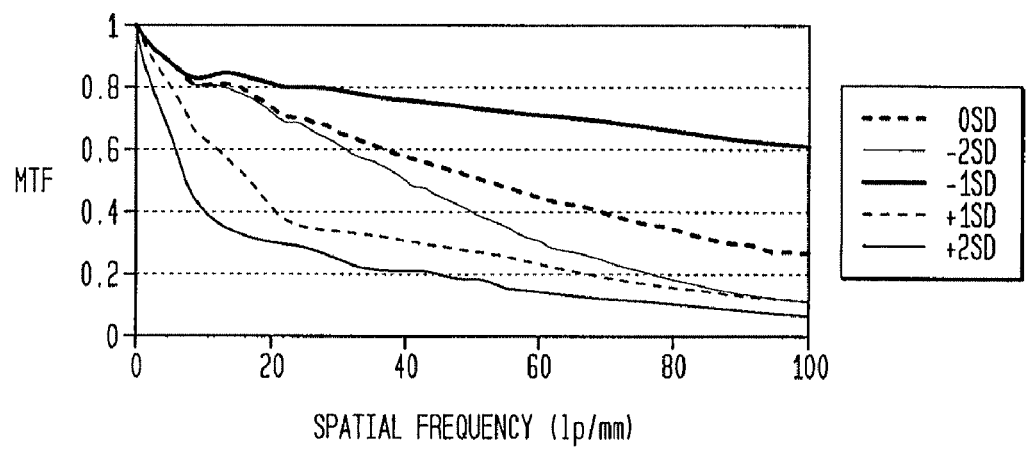
FIG. 4A shows a plurality of MTFs calculated in an exemplary embodiment of a method of the invention for a plurality of eye models characterized by different values of corneal sphericity, in which a hypothetical IOL design was incorporated.
Figure 4B:
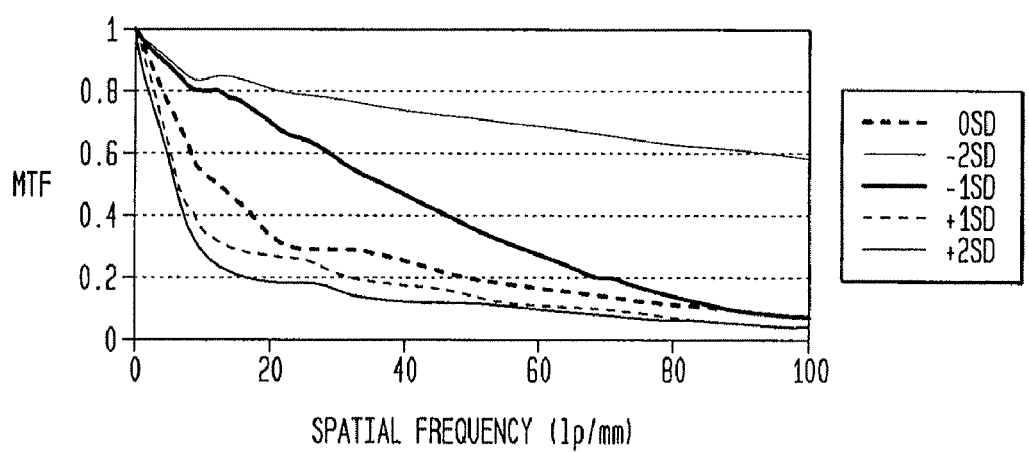
FIG. 4B shows a plurality of MTFs calculated in an exemplary embodiment of a method of the invention for a plurality of eye models characterized by different values of corneal sphericity, in which another (reference) hypothetical IOL was incorporated.

By way of example, FIG. 4A shows the MTFs calculated for eye models characterized by five different values of corneal asphericity (i.e., −0.503 (−2 SD), −0.343 (−1 SD), −0.183 (0 SD), −0.023 (+1 SD) and +0.137 (+2 SD)), in which the above hypothetical IOL identified as Design #3 was incorporated. A constant corneal radius of 7.72 mm was selected for each eye model. FIG. 4B shows similarly calculated MTFs for the above eye models, in which the above hypothetical IOL designated as reference was incorporated. The calculations presented in FIGS. 4A and 4B were performed for a 6.0 mm entrance pupil (5.2 mm at IOL plane).

The above simulations of the performance of a hypothetical aspherical and a hypothetical spherical lens as a function of the corneal asphericity show that the aspherical lens performs better than the spherical lens for a variety of corneal asphericities except for an aberration-free cornea. However, only a small percentage of the eyes in the general population exhibit an aberration-free cornea (about 6%), and even for such eyes, the performance of the aspherical lens is reasonably good.

Figure 5A:
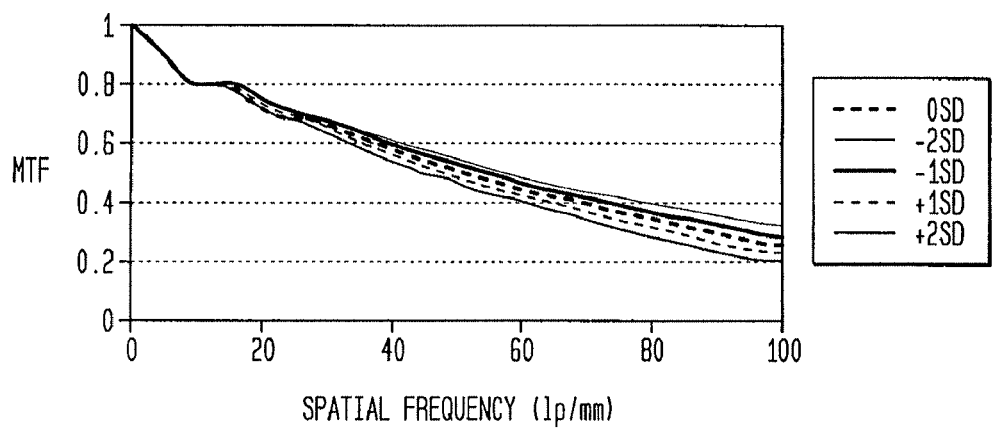
FIG. 5A shows a plurality of MTFs calculated in an exemplary embodiment of a method of the invention for a plurality of eye models characterized by different values of anterior chamber depth, in which a hypothetical IOL design was incorporated.
Figure 5B:
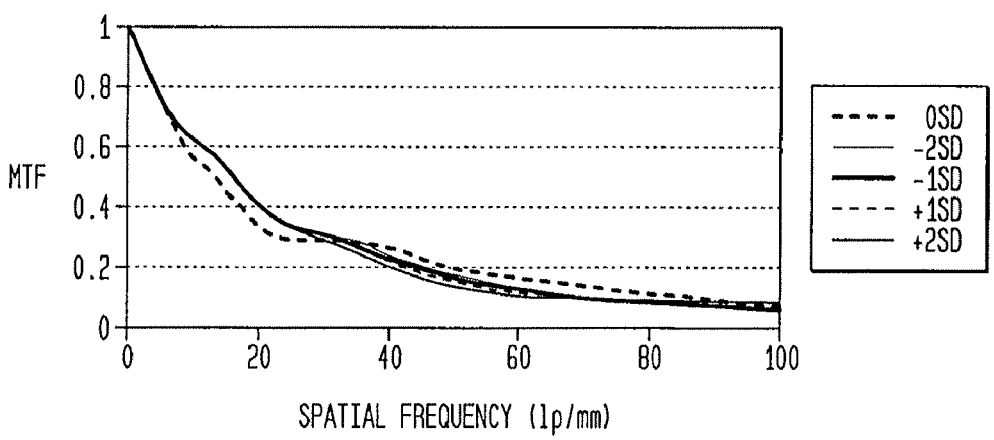
FIG. 5B shows a plurality of MTFs calculated in an exemplary embodiment of a method of the invention for a plurality of eye models characterized by different values of anterior chamber depth, in which a different (reference) hypothetical IOL was incorporated.

The anterior chamber depth, defined as the distance between the anterior corneal surface and the anterior lens surface, is another parameter whose variations in a population can be considered in simulating the performance of a plurality of IOLs. By way of example, FIG. 5A presents a plurality of MTFs calculated for eye models characterized by the following values of anterior chamber depth, in which the above hypothetical IOL identified as Design #3 was incorporated: 4.0 mm (−2 SD), 4.3 mm (−1 SD), 4.6 mm (0 SD), 4.9 mm (+1 SD), and 5.2 mm (+2 SD). To compare the performance of the Design #3 lens with that of the reference lens as a function of variations in the anterior chamber depth, similar MTFs were computed for the above eye models in which the reference lens was incorporated, as shown in FIG. 5B. For both sets of calculations, a 6.0 mm pupil was employed.

These simulations indicate that the optical performances of the two IOLs (aspherical and spherical) are less susceptible to variations in anterior chamber depth than in corneal asphericity and/or radius. Although a deviation of an implanted IOL's position at an anterior chamber depth from its intended design position can theoretically affect the residual spherical aberration and astigmatic error, the above calculations indicate that such residual errors can be quite limited in practice.

Figure 6:
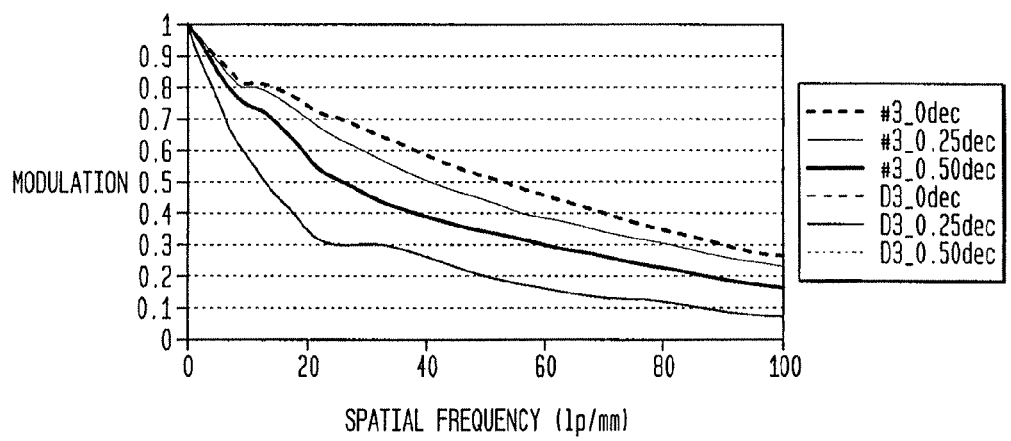
FIG. 6 presents a plurality of MTFs calculated for eye models, in one of which a reference IOL and in the other a hypothetical IOL design were incorporated, as a function of different decentration values of the IOLs.

Other parameters that can affect the optical performance of a lens include misalignment effects, such as decentration, tilt and rotation. A lens placed in the human eye can be subject to these misalignments relative to the cornea. For example, the performance of an aspherical lens can be adversely affected due to decentration and tilt. Further, the performance of a toric lens can be susceptible to lens rotation, e.g., the lens rotation can cause astigmatic error. By way of example, FIG. 6 presents MTFs calculated for model eyes, in one of which the above hypothetical aspherical lens designated as Design #3 and in the other the above hypothetical spherical reference lens were incorporated, as a function of the following decentration values: 0.0 mm, 0.25 mm and 0.5 mm. The calculations were performed for a 6.0 mm entrance pupil (5.2 mm at the IOL plane). These simulations indicate that the aspherical lens is more susceptible to decentration than the spherical lens. However, even with a 0.5 mm decentration, the aspherical lens performs better than the spherical lens.

Figure 7:
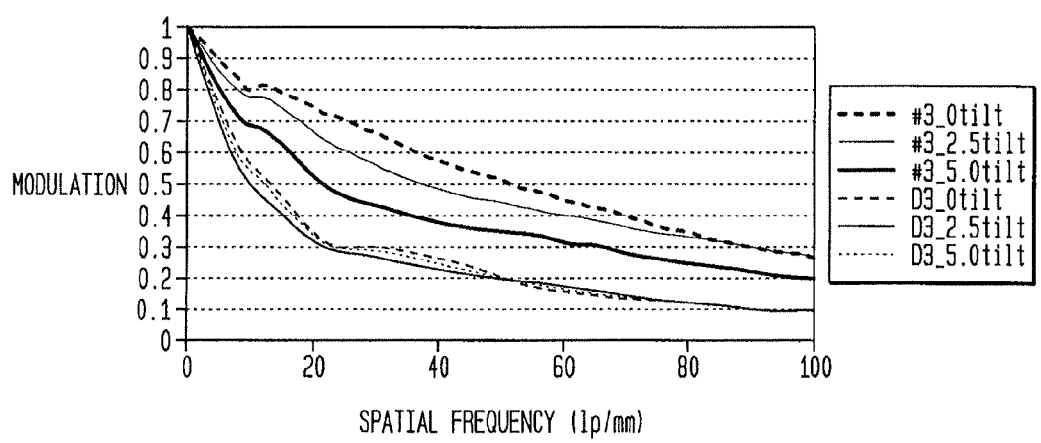
FIG. 7 presents a plurality of MTFs calculated for eye models, in one of which a reference IOL and in the other a hypothetical IOL design were incorporated, as a function of different tilt values of the IOLs.

By way of further illustration, similar MTF calculations were performed on the two aforementioned aspherical and spherical lenses (i.e., Design #3 and reference) for the following tilt angles (at a pupil size of 6.0 mm): 0, 2.5 and 5. These calculations, which are presented in FIG. 7, indicate that performance of the aspherical lens is more susceptible to the lens tilt than that of the spherical lens. However, the aspherical lens outperforms the spheric lens for all of the tilt angles.

Figure 8:
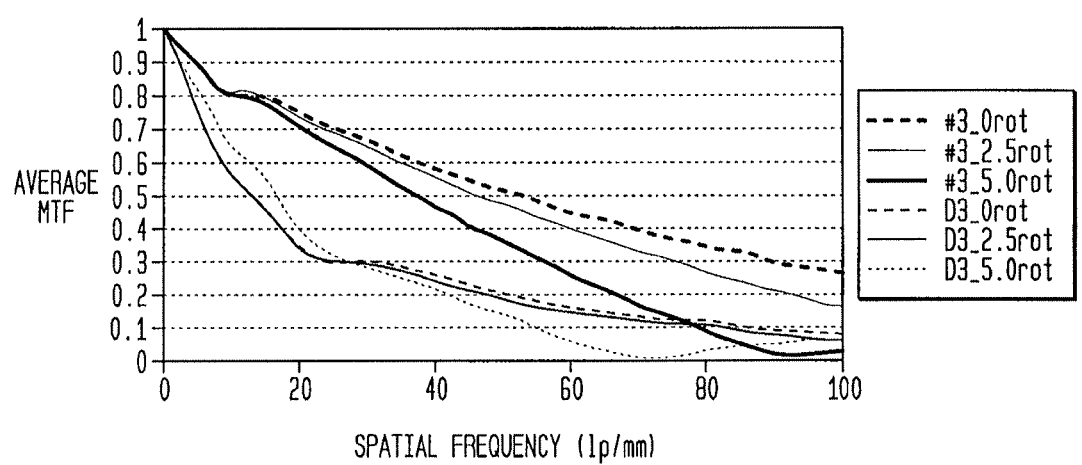
FIG. 8 presents a plurality of MTFs calculated for eye models having a hypothetical aspheric/toric IOL design and a reference spherical/toric IOL for three rotation angles of the lenses.

The lens rotation within the eye can also affect its optical performance, e.g., by introducing residual astigmatism. By way of example, FIG. 8 presents a plurality of MTFs calculated for model eyes having the above hypothetical aspheric/toric Design #3 lens as well as the spherical/toric reference lens for the following lens rotations angles (at a pupil size of 6.0 mm): 0°, 2.5° and 5°. These simulations indicate that the aspherical lens generally performs better than the spherical lens. In particular, the images generated by the aspherical lens exhibit significantly higher contrast over a wide range of spatial frequencies, even under a considerable lens rotation of 5°.

Figure 9A:
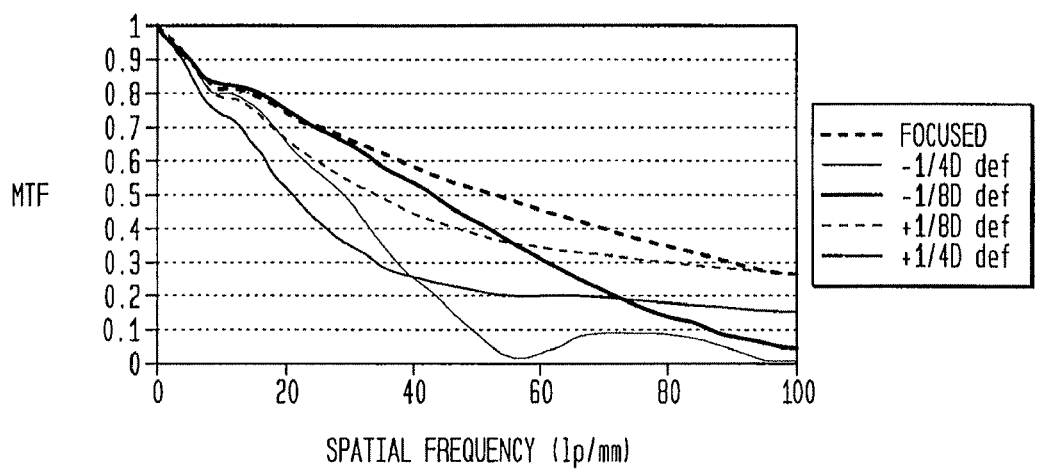
FIG. 9A shows exemplary MTF calculations performed in an embodiment of a method of the invention for eye models having a hypothetical IOL design for a number of different spherical refractive errors.
Figure 9B:
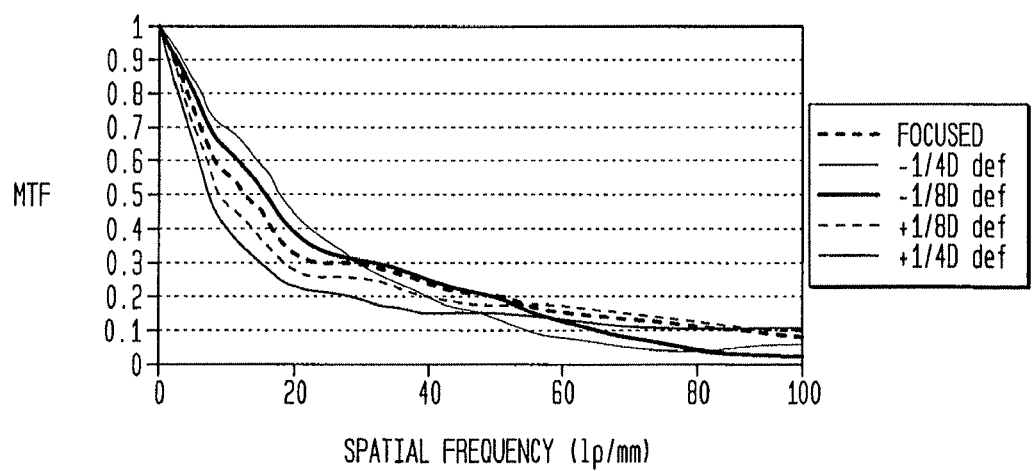
FIG. 9B shows exemplary MTF calculations performed in an embodiment of a method of the invention for eye models having a reference IOL for a number of different spherical refractive errors.

Refractive errors, which can give rise to defocus, constitute another set of parameters that can be utilized in simulating the optical performance of IOLs. For example, with current surgical techniques, spherical and/or cylindrical refractive errors of the order of +/−¼ D can occur. FIGS. 9A and 9B show, respectively, exemplary MTF calculations performed for model eyes with the above Design #3 as well as the reference hypothetical lens for the following spherical refractive errors: 0 D, ±⅛ D, and ±¼ D (a pupil size of 6.0 mm was assumed). These calculations indicate that the performance of the aspherical lens can be more susceptible to spherical refractive errors. However, when considering the absolute magnitudes of modulation contrasts, the aspherical lens performs better up to a defocus of about ¼ D.

Figure 10:
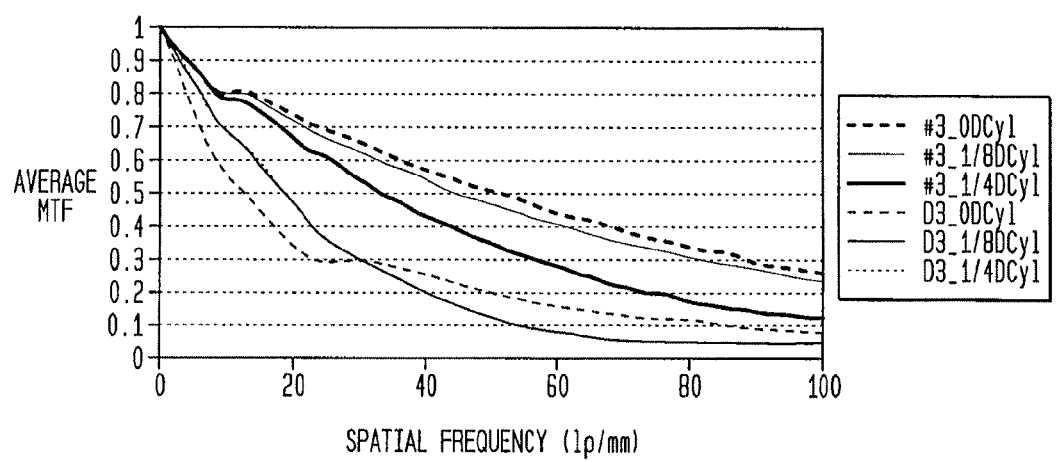
FIG. 10 presents MTFs computed for eye models having a reference IOL and a hypothetical design IOL for a number of different cylindrical refractive errors.

By way of further examples, FIG. 10 presents MTFs computed for model eyes having the above Design #3 lens and the reference hypothetical lens as a function of the following cylindrical refractive errors (at a pupil size of 6.0 mm): 0 D, ±⅛, and ±¼ D). These simulations indicate that cylindrical refractive errors cause similar MTF drops for the spherical and the aspherical lenses. However, even with a ¼ D cylindrical error, the aspherical lens exhibits a substantially greater MTF relative to that exhibited by the spherical lens with no cylindrical error. It should be noted that misalignments due to lens rotation, which were discussed above, can also induce residual cylindrical errors. However, the lens rotation can induce higher-order aberrations, as well.

Another parameter that can play a role in the optical performance of an IOL is the effective location of that IOL in the eye. Hence, in some embodiments of the invention, variations in the location of the $2^{nd}$ principal plane of an implanted IOL are simulated to take into account refractive errors that such variations can induce.

Figure 11:
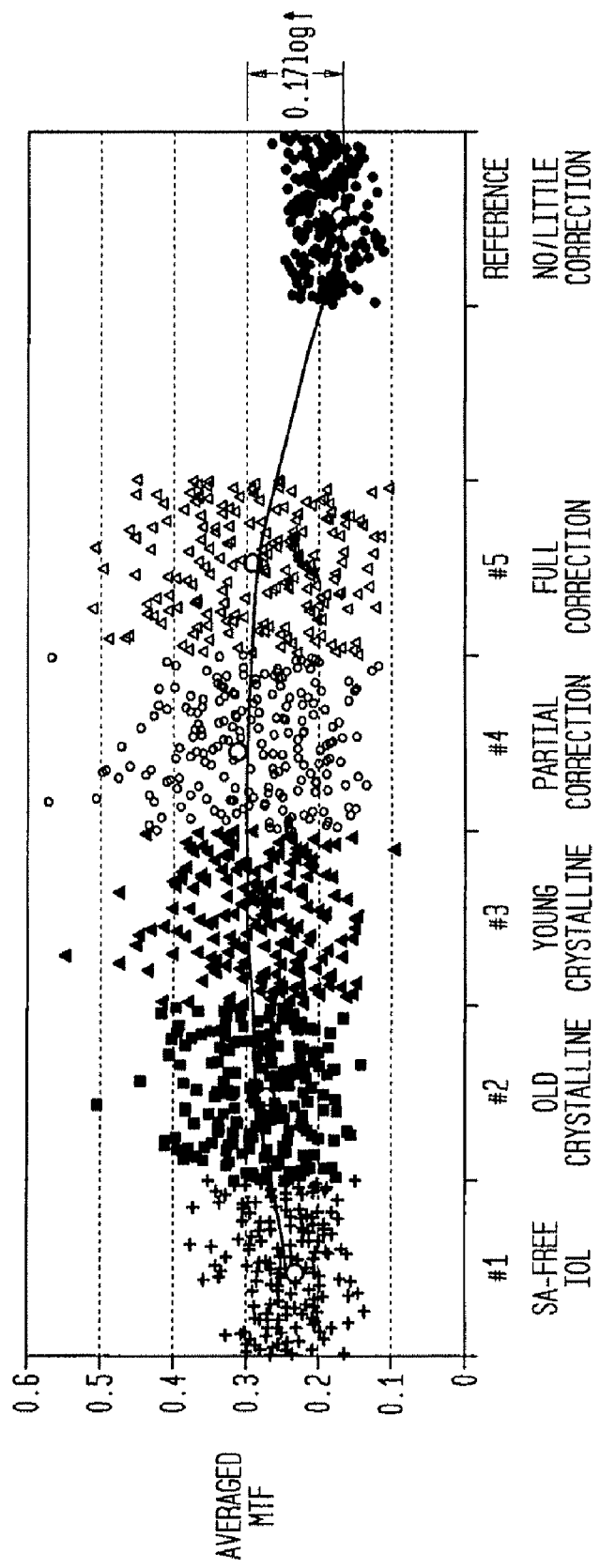
FIG. 11 shows the results of simulations of averaged MTF for 200 eye models, characterized by different biometric parameters and/or misalignment and refractive errors, where each eye model was considered with six different hypothetical IOLs, FIG. 12 graphically depicts a change in the MTF associated with each simulated eye model in FIG. 11, in response to replacing a spherical reference lens in the model with one of a number of different aspherical lenses, FIG. 13 graphically depicts the distribution of calculated MTF values corresponding to different simulated eye models in which a plurality of IOL design options were incorporated, FIG. 14 schematically depicts an offset between a line of sight associated with a model eye and an optical axis of an IOL incorporated in the model eye.

FIG. 11 shows the results of simulations of 200 eye models, characterized by different biometric parameters and/or misalignment and refractive errors, with each of the above hypothetical IOLs (Table 1). The MTF for each simulation is presented as a data point. The average MTF, the 10, 50 and 90 percentiles, as well as standard deviation (SD) and +/−2 SD deviations from the mean are presented in Table 2 below:

TABLE 2

|  | 10% | 50% | 90% | Mean | Std | Mean − 2 * SD | Mean + 2 * SD |
| --- | --- | --- | --- | --- | --- | --- | --- |
| Design #1 | 0.303 | 0.243 | 0.189 | 0.244 | 0.047 | 0.149 | 0.339 |
| Design #2 | 0.378 | 0.269 | 0.2 | 0.278 | 0.065 | 0.148 | 0.409 |
| Design #3 | 0.381 | 0.275 | 0.188 | 0.28 | 0.076 | 0.128 | 0.431 |
| Design #4 | 0.409 | 0.277 | 0.184 | 0.288 | 0.089 | 0.11 | 0.466 |
| Design #5 | 0.415 | 0.276 | 0.169 | 0.284 | 0.093 | 0.098 | 0.469 |
| Reference | 0.232 | 0.192 | 0.145 | 0.19 | 0.033 | 0.124 | 0.256 |

The average MTF initially increases with an increase in the aspherical correction exhibited by the lens designs to reach a plateau, and then declines. In fact, the design option providing a substantially complete spherical aberration correction does not provide the best overall optical performance across the whole population. Rather, the average MTF peaks when the lens partially corrects the corneal spherical aberration. The spread of optical performance within the simulated population also increases as the amount of spherical aberration correction provided by the lens designs increases. In particular, an increase in the amount of spherical aberration correction results in over-correction for an increasing percentage of the population while providing benefits for more patients with aberrated corneas. Regardless, all of the aspherical design options (#1 to #5) provide considerable advantages over the spherical reference design.

Figure 12:
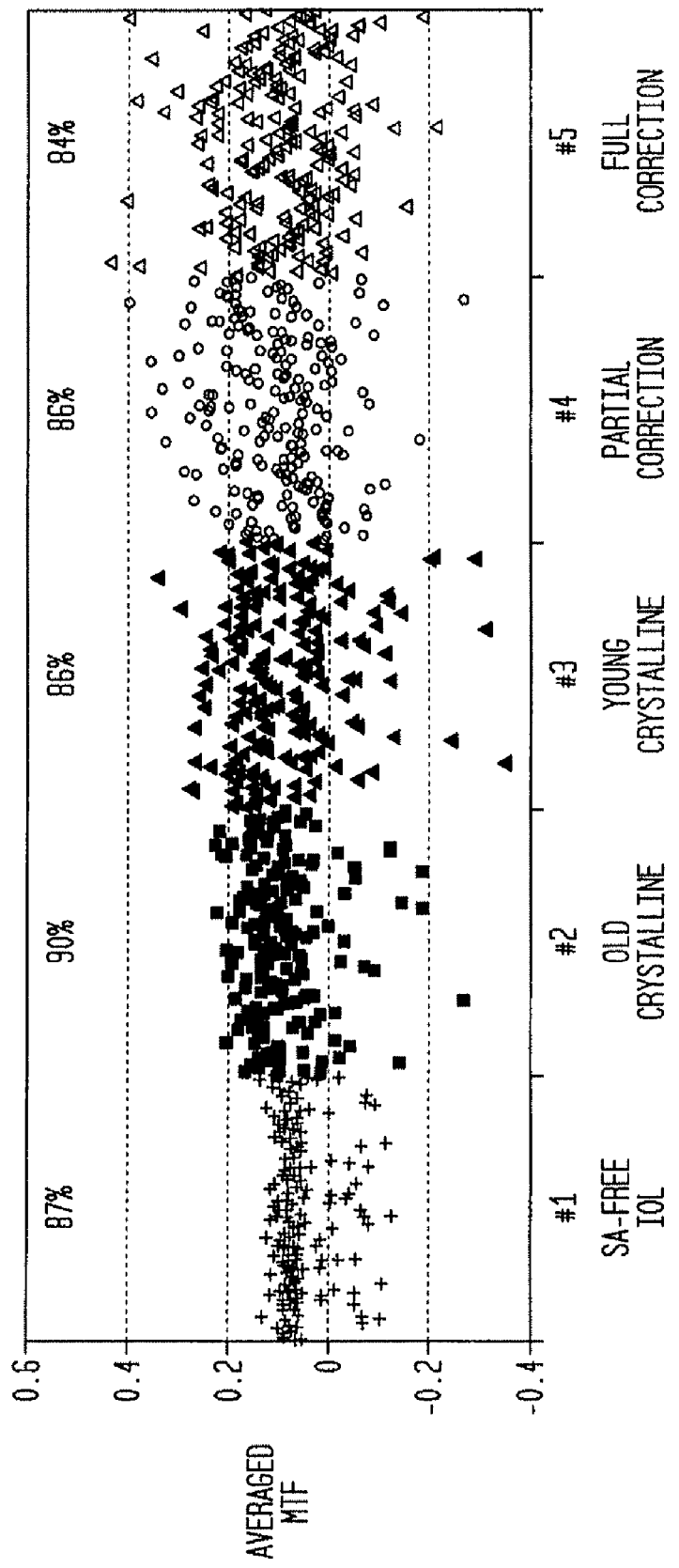

FIG. 12 graphically depicts a change in the MTF associated with each simulated eye in response to replacing the spherical reference lens with one of the aspherical lenses. The percentage of eye models (simulated patients) that benefit from an aspherical design can be calculated by counting the number of eye models that exhibit an improvement in their respective MTFs. The aspherical designs generally exhibit an improved optical performance relative to the spherical design for the majority of the eye models. For example, the percentage of the eye models that benefit from the design options #1 through #5 in the above simulations ranges from about 84% to about 90%, with the design options #1 through #3 providing the more pronounced improvements.

Similar Monte Carlo simulations were performed for the above hypothetical lenses for an entrance pupil size of 4.5 mm. As in the previous simulations, 200 eye models were considered for each lens design option. Table 3 below lists the results of these simulations in terms of average MTF, the 10, 50 and 90 percentiles, as well as standard deviation (SD) and ±2 SD deviations from the mean:

TABLE 3

| | 10% | 50% | 90% | Mean | Std | Mean − 2 * Std | Mean + 2 * Std |
|---|---|---|---|---|---|---|---|
| Design #1 | 0.413 | 0.342 | 0.263 | 0.342 | 0.06 | 0.222 | 0.504 |
| Design #2 | 0.46 | 0.363 | 0.261 | 0.356 | 0.072 | 0.212 | 0.496 |
| Design #3 | 0.47 | 0.355 | 0.265 | 0.362 | 0.079 | 0.204 | 0.486 |
| Design #4 | 0.473 | 0.336 | 0.242 | 0.345 | 0.089 | 0.167 | 0.423 |
| Design #5 | 0.439 | 0.332 | 0.228 | 0.332 | 0.079 | 0.174 | 0.427 |
| Reference | 0.307 | 0.25 | 0.166 | 0.243 | 0.054 | 0.136 | 0.325 |

Figure 13:
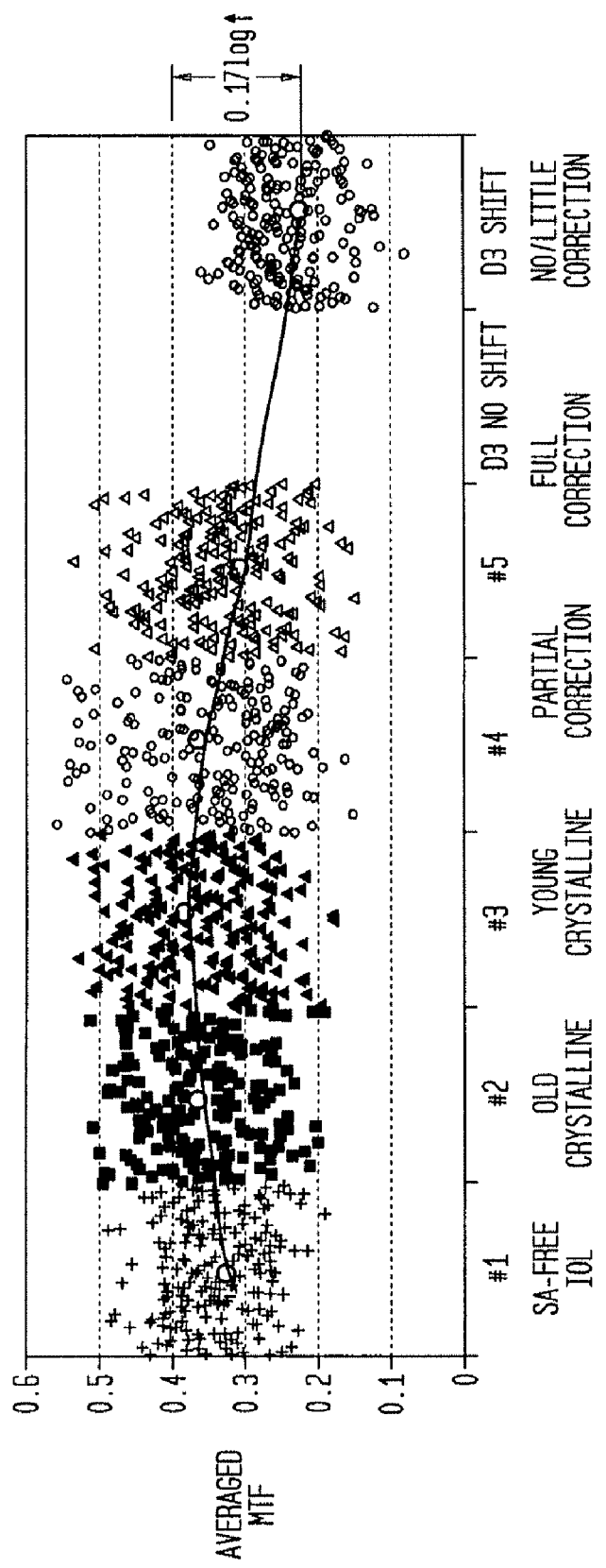

FIG. 13 shows the distribution of the MTF values corresponding to different simulated eye models in which the above lens options were incorporated. Further, Table 4 below provides a summary of MTF improvement and percentage of simulated eyes benefiting from each aspherical design relative to the spherical reference lens:

TABLE 4

| | 4.5 mm pupil | | 6.0 mm pupil | |
|---|---|---|---|---|
| | %(log) improvement | % of benefited population | %(log) improvement | % of benefited population |
| Design #1 | 41% | 83% | 28% | 87% |
| Design #2 | 47% | 85% | 47% | 90% |
| Design #3 | 49% | 89% | 47% | 86% |
| Design #4 | 42% | 87% | 52% | 86% |
| Design #5 | 37% | 85% | 49% | 84% |

These simulations suggest that Design #3 provides the best average optical performance, with the maximum percentage of simulated patient satisfaction (as measured by the MTF). In particular, the average MTF associated with Design #3 is greater by about 0.17 log unit relative to that of the reference lens, with up to about 89% of the simulated eye models exhibiting better performance with Design #3 than with the reference lens.

In some embodiments, the simulations of the model eyes can be utilized to select one or more lens Designs as providing the best fit for a population of interest, for example, based on the average MTF computed for the simulated eyes and/or the percentage of simulated eyes that exhibit improved performance relative to a reference. For example, the above simulations for a 4 mm pupil can be utilized to select Design options #2, #3 and #4 as providing a greater average MTF as well as a higher percentage of simulated eyes exhibiting improved performance relative to the reference lens. For the simulations employing a 6 mm pupil size, the Design options #3, #4, and #5 can be selected based on MTF improvement and Design options #1, #2 and #3 can be selected based on increase in percentage of the simulated eyes exhibiting improved performance. In all cases, the Design option #3 provides superior optical performance and spherical correction robustness.

In some embodiments, a family of IOL designs can be selected, based on evaluation of the optical performance of a plurality of IOL designs, such that each selected IOL design provides the best fit visual performance (e.g., visual acuity, contrast sensitivity or a combination thereof) for a portion of a population of patient eyes. By way of example, an IOL design exhibiting an spherical aberration of about −0.1 microns can be selected for patients within one portion of the population while two other IOL designs, one exhibiting an spherical aberrations of about −0.2 micron and the other exhibiting an spherical aberration of about −0.3 microns, can be selected for two other portions of the population.

The visual performance of an IOL can be evaluated based on any appropriate criterion (e.g., based on visual acuity, contrast sensitivity or a combination of the two). In some embodiments, the optical performance of an IOL design is modeled (evaluated) by utilizing MTF values at low spatial frequencies to model contrast sensitivity obtained by that IOL and employing MTF values at high spatial frequencies to model visual acuity obtained by that IOL. By way of example, spatial frequencies less than about 60 lp/mm (~18 cycles/ degree) (e.g., in a range of about 5 to about 60 lp/mm (~1.5 to 18 cycles/degree)) can be employed to evaluate contrast sensitivity exhibited by a model eye in which an IOL design is incorporated while spatial frequencies greater than about 60 lp/mm (~18 cycles/degree) (e.g. in a range of about 60 to about 100 lp/mm (~18 to 30 cycles/degree)) can be employed to evaluate visual acuity exhibited by that model eye.

In some embodiments, manufacturing tolerances can be considered in simulating the performance of an IOL in a model eye. By way of example, manufacturing tolerances corresponding to lens surface radius and asphericity, lens surface irregularity, lens surface centration and tilt, lens thickness and toric tolerance can be taken into account to determine an optimal IOL for implantation in eyes of patients within a population of interest. For example, in Monte Carlo simulations, one or more of such tolerances (e.g., in addition to the biometric parameters discussed above) can be varied over a range typically observed in manufacturing of a lens of interest so as to model their contributions to the performance of one or more lens designs. The lens design exhibiting the best performance can then be selected as the most suitable for use in the population of interest.

Figure 14:
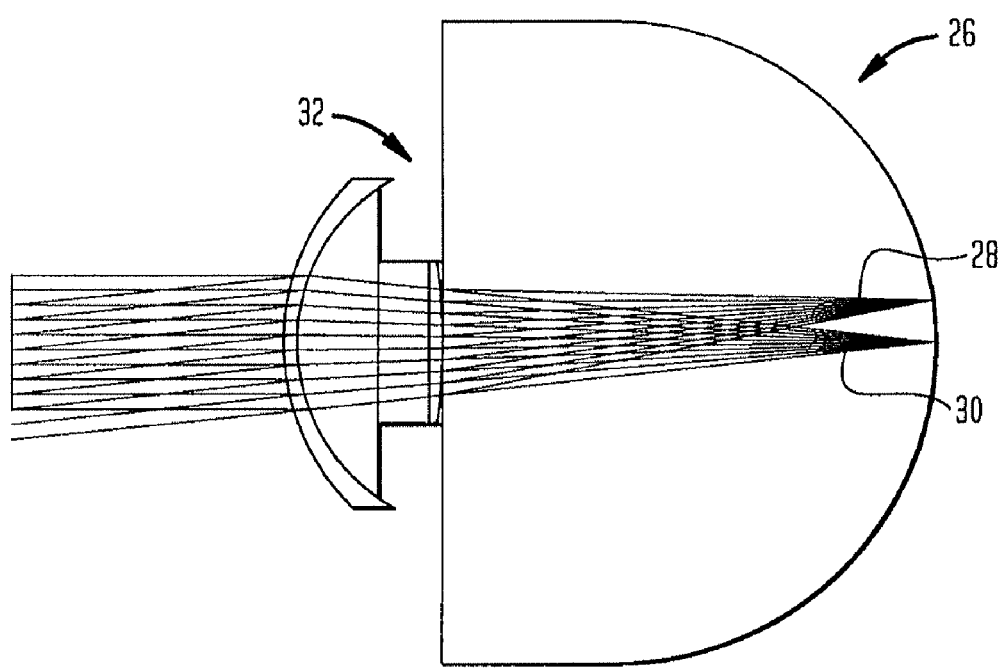

When an IOL is implanted in a patient's eye, the IOL's optical axis can be offset (e.g., due to tilt and/or decentration) relative to an axis associated with the eye's line of sight. Hence, in some embodiments, the effects of such offset are considered in simulating the performance of a plurality of IOLs incorporated in model eyes. By way of example, as shown schematically in FIG. 14, the line of sight of an eye model 26 can be associated with a set of rays 28 that are offset relative to a set of rays 30 incident on an IOL 32, which is incorporated in the model eye, parallel to the IOL's optical axis.

Figure 15A:
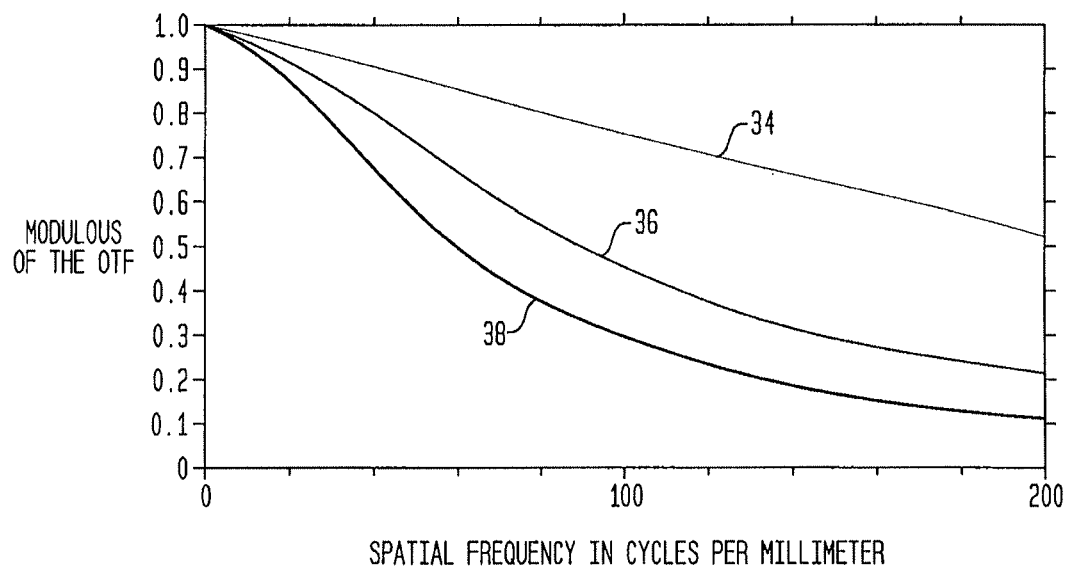
FIG. 15A presents a plurality of polychromatic MTFs calculated for a model eye in which an aspherical lens is incorporated for a zero tilt and a 5-degree tilt of the optical axis of the lens relative to the line of sight of the eye.
Figure 15B:
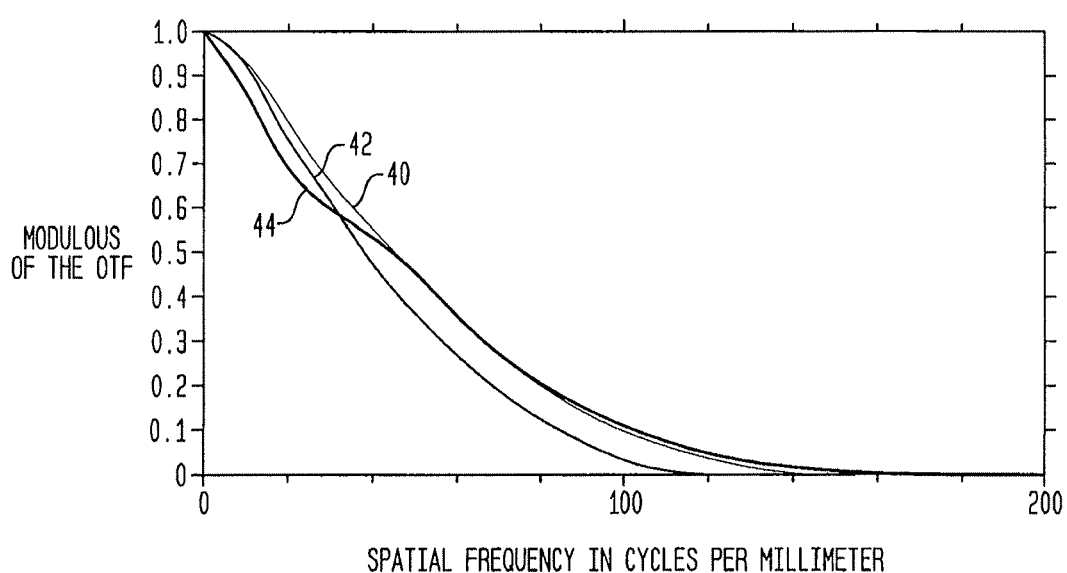
FIG. 15B presents a plurality of polychromatic MTFs calculated for a model eye in which a spherical lens is incorporated for a zero tilt and a 5-degree tilt of the optical axis of the lens relative to the line of sight of the eye.

By way of illustration, FIGS. 15A and 15B compare the optical performance of two lenses, one having an aspherical surface and the other spherical surfaces, incorporated in an average model eye as a function of a 5-degree tilt relative to the eye's line of sight. More specifically, FIG. 15A presents polychromatic (incident light having wavelengths of 450 nm, 550 nm, and 650 nm) MTF curves 34, 36 and 38, calculated at the retinal plane of the model eye with a 5-mm pupil in which the aspherical lens having a surface asphericity characterized by a conic constant of about −42 was incorporated. The curve 34 corresponds to zero tilt, while the curves 36 and 38, in turn, provide MTF values along two orthogonal directions for a case in which the optical axis of the lens is tilted by about 5-degrees relative to the line of sight associated with the model eye. FIG. 15B also provides three polychromatic MTF curves 40, 42, and 44, where the curve 40 corresponds to zero tilt between the optical axis of the spherical lens relative to the eye's line of sight while the curves 42 and 44 provide MTF values along two orthogonal directions for a case in which the optical axis of the IOL exhibits a 5-degree tilt relative to the eye's line of sight. A comparison of the MTF curves presented by FIGS. 15A and 15B indicates that although the tilt can have a greater affect on the performance of the aspherical IOL, the aspherical IOL provides a considerably enhanced contrast relative to the spherical IOL.

Figure 16A:
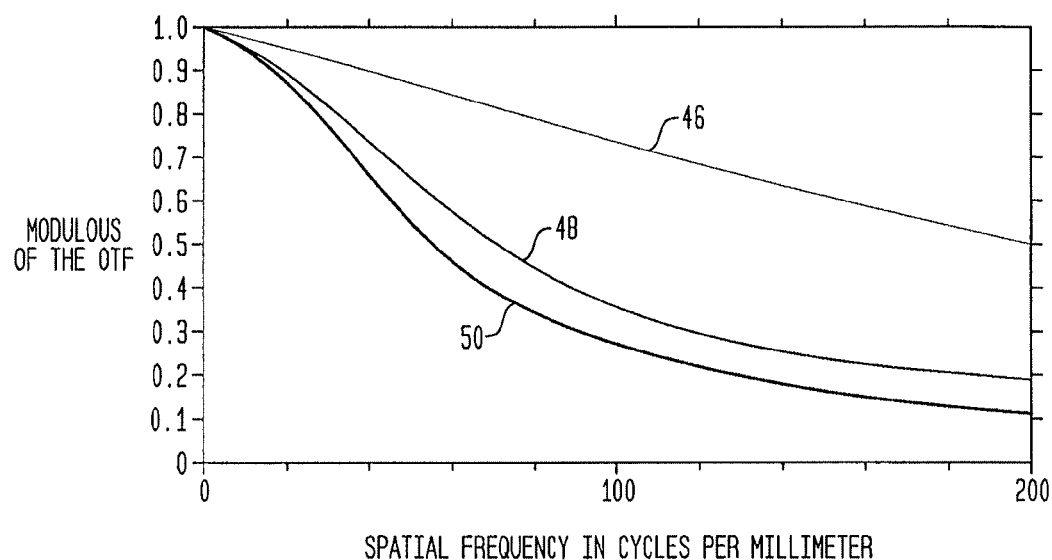
FIG. 16A presents a plurality of polychromatic MTFs calculated for a model eye in which an aspherical lens is incorporated for a zero tilt and decentration and a 5-degree tilt and a 0.5-mm decentration of the optical axis of the lens relative to the line of sight of the eye.
Figure 16B:
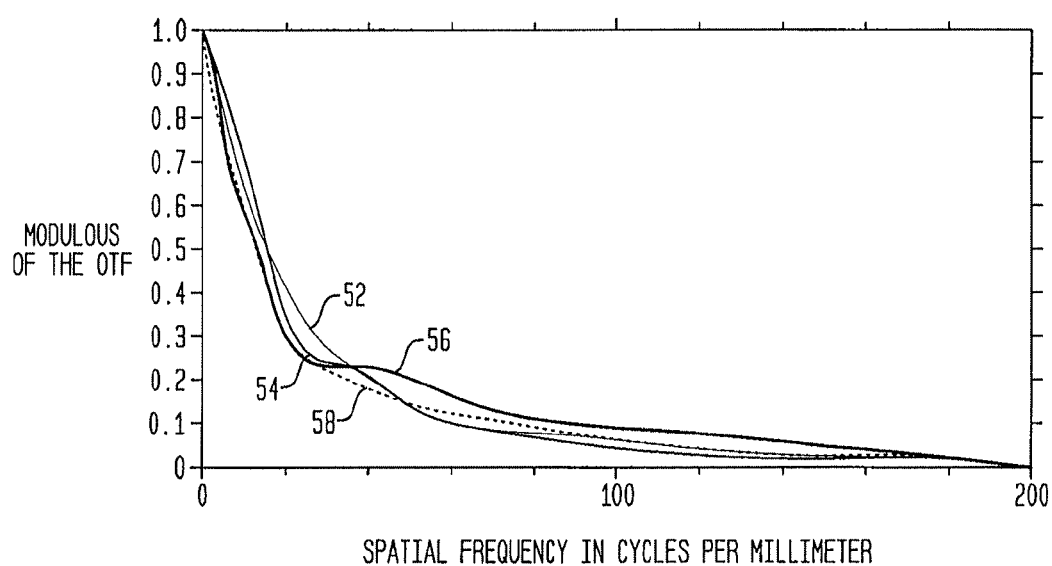
FIG. 16B presents a plurality of polychromatic MTFs calculated for a model eye in which a spherical lens is incorporated for a zero tilt and decentration and a 5-degree tilt and a 0.5-mm decentration of the optical axis of the lens relative to the line of sight of the eye.

The offset of an IOL's optical axis relative to a patient's eye line of sight can be due not only to a tilt but also a decentration of the IOL. By way of illustration, FIG. 16A presents respective polychromatic MTF curves 46, 48, and 50 calculated at the retina of an average model eye with a 5-mm pupil in which an aspherical IOL, characterized by a conic constant of about −27, was incorporated. The curve 46 is a reference MTF corresponding to zero tilt and decentration while curves 48 and 50 present MTF values along two orthogonal directions corresponding to a 5-degree tilt and a 0.5-mm displacement of the IOL's optical axis relative to the pupil's center. FIG. 16B presents, in turn, MTF curves 52, 54, 56 and 58 calculated at the retina of an average model eye in which a spherical IOL was incorporated. The curves 52 and 54 are reference MTFs corresponding to zero tilt and decentration of the IOL's optical axis relative to the model eye's line of sight while the curves 56 and 58 provide MTF values along two orthogonal directions corresponding to a 5-degree tilt and a 0.5-mm decentration. (i.e., a displacement of the optical axis of the IOL relative to the center of the pupil). A comparison of the MTFs presented in FIGS. 16A and 16B indicates that the aspherical IOL provides a better optical performance than the spherical IOL for the assumed tilt and decentration values.

More generally, in many embodiments of the invention, an asphericity characterized by a conic constant in a range of about −73 to about −27 can be imparted to at least one surface of the IOL to ensure a more robust performance in presence of an offset of the line of sight relative to an optical axis of an IOL. By way of example, a most suitable value of the asphericity for a patient population can be obtained, e.g., by evaluating optical performance of lenses with different values of asphericity (e.g., by performing Monte Carlo simulations) for a range of typically observed offset values.

Those having ordinary skill in the art will appreciate that various changes can be made to the above embodiments without departing from the scope of the invention.

What is claimed is:

1. A method of manufacturing an ophthalmic lens, comprising
    establishing a model eye that incorporates a plurality of ophthalmic lens designs,
    determining a modulation transfer function (MTF) at a retinal plane of said model eye,
    utilizing at least one MTF value corresponding to a low spatial frequency to evaluate a contrast sensitivity of said model eye;
    selecting the ophthalmic lens design with the highest contrast sensitivity; and
    manufacturing at least one ophthalmic lens according to the selected ophthalmic lens design.

2. The method of claim 1, wherein said low spatial frequency is less than about 60 lp/mm (~18 cycles/degree).

3. The method of claim 2, wherein said low spatial frequency lies in a range of about 5 to about 60 lp/mm (~1.5 to 18 cycles/degree).

4. The method of claim 1, further comprising utilizing at least one MTF value corresponding to a high spatial frequency to evaluate visual acuity of said model eye.

5. The method of claim 4, wherein said high spatial frequency is greater than about 60 lp/mm (~18 cycles/degree).

6. The method of claim 5, wherein said high spatial frequency is in a range of about 60 to about 100 lp/mm (~18 to 30 cycles/degree).

7. The method of claim 1, wherein said ophthalmic lens comprises an intraocular lens.

8. A method of manufacturing an ophthalmic lens, comprising
    establishing a model eye that incorporates a plurality of ophthalmic lens designs,
    determining a modulation transfer function (MTF) at a retinal plane of the model eye,
    utilizing at least one MTF value corresponding to a high spatial frequency to evaluate a visual acuity of said model eye,
    selecting the ophthalmic lens design with the highest visual acuity; and
    manufacturing at least one ophthalmic lens according to the selected ophthalmic lens design.

9. The method of claim 8, wherein said high spatial frequency is greater than about 60 lp/mm (~18 cycles/degree).

10. The method of claim 9, wherein said high spatial frequency is in a range of about 60 to about 100 lp/mm (~18 to 30 cycles/degree).

* * * * *